(12) United States Patent
Chen et al.

(10) Patent No.: US 9,987,099 B2
(45) Date of Patent: Jun. 5, 2018

(54) DISPOSABLE HOUSINGS FOR ENCASING HANDLE ASSEMBLIES

(71) Applicant: Covidien LP, Mansfield, MA (US)

(72) Inventors: Xingrui Chen, Hamden, CT (US); Matthew Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 531 days.

(21) Appl. No.: 14/674,152

(22) Filed: Mar. 31, 2015

(65) Prior Publication Data

US 2015/0366560 A1 Dec. 24, 2015

Related U.S. Application Data

(60) Provisional application No. 62/013,607, filed on Jun. 18, 2014.

(51) Int. Cl.
*A61B 17/00* (2006.01)
*A61B 17/072* (2006.01)
(Continued)

(52) U.S. Cl.
CPC .............. *A61B 90/90* (2016.02); *A61B 17/00* (2013.01); *A61B 17/072* (2013.01); *A61B 90/92* (2016.02); *A61B 46/10* (2016.02); *A61B 46/13* (2016.02); *A61B 2017/0023* (2013.01); *A61B 2017/0046* (2013.01); *A61B 2017/00398* (2013.01); *A61B 2017/00464* (2013.01); *A61B 2017/00473* (2013.01); *A61B 2017/00477* (2013.01); *A61B 2017/00482* (2013.01); *A61B 2017/00486* (2013.01); *A61B 2017/0688* (2013.01);
(Continued)

(58) Field of Classification Search
CPC ......... A61B 90/90; A61B 90/92; A61B 90/94; A61B 90/96; A61B 2017/0023; A61B 2017/0046; A61B 2017/00464; A61B 2017/00469; A61B 2017/00473; A61B 2017/00477; A61B 2017/00482; A61B 2017/00526; A61B 17/068; A61B 17/072
See application file for complete search history.

(56) References Cited

U.S. PATENT DOCUMENTS 5,275,612 A 1/1994 Bales, Jr.
5,314,406 A * 5/1994 Arias ................. A61B 17/3203
604/167.04
(Continued)

FOREIGN PATENT DOCUMENTS

WO 03/020148 A1 3/2003
WO 2009039506 A1 3/2009

OTHER PUBLICATIONS

European Communication dated Jan. 25, 2017, corresponding to European Application No. 15172511.6; 5 pages.
(Continued)

*Primary Examiner* — Stephen F Gerrity
*Assistant Examiner* — Joshua Kotis

(57) ABSTRACT

A disposable housing includes a housing portion and a memory. The housing portion defines a cavity therein configured to receive a motor operable, inner core handle assembly. At least a portion of the housing portion has a color that corresponds to a color of one type of end effector or adapter assembly. The memory has stored therein at least one operating parameter for the inner core handle assembly.

11 Claims, 5 Drawing Sheets

(51) Int. Cl.
  *A61B 90/90* (2016.01)
  *A61B 90/92* (2016.01)
  *A61B 17/068* (2006.01)
  *A61B 17/29* (2006.01)
  *A61B 46/13* (2016.01)
  *A61B 46/10* (2016.01)

(52) U.S. Cl.
  CPC ............... *A61B 2017/07271* (2013.01); *A61B 2017/2925* (2013.01)

(56) References Cited

U.S. PATENT DOCUMENTS

| | | | |
|---|---|---|---|
| 5,322,161 A | | 6/1994 | Shichman et al. |
| 5,331,971 A | * | 7/1994 | Bales ................... A61B 10/06 600/562 |
| 5,356,064 A | | 10/1994 | Green et al. |
| 5,391,144 A | * | 2/1995 | Sakurai ............ A61B 17/22012 601/3 |
| 5,400,267 A | * | 3/1995 | Denen ................. A61B 17/00 128/908 |
| 5,573,529 A | | 11/1996 | Haak et al. |
| 5,651,780 A | | 7/1997 | Jackson et al. |
| 5,693,042 A | | 12/1997 | Boiarski et al. |
| 5,993,470 A | | 11/1999 | Yoon |
| 6,099,537 A | * | 8/2000 | Sugai ................. A61B 17/0684 606/143 |
| 6,223,440 B1 | | 5/2001 | Rashman |
| 6,264,087 B1 | | 7/2001 | Whitman |
| 6,315,184 B1 | | 11/2001 | Whitman |
| 6,348,061 B1 | | 2/2002 | Whitman |
| 6,443,973 B1 | | 9/2002 | Whitman |
| 6,488,197 B1 | | 12/2002 | Whitman |
| 6,491,201 B1 | | 12/2002 | Whitman |
| 6,533,157 B1 | | 3/2003 | Whitman |
| 6,668,751 B1 | | 12/2003 | Henke |
| 6,716,233 B1 | | 4/2004 | Whitman |
| 7,905,886 B1 | | 3/2011 | Curran et al. |
| 7,931,660 B2 | | 4/2011 | Aranyi et al. |
| 8,444,662 B2 | | 5/2013 | Palmer et al. |
| 8,490,850 B2 | | 7/2013 | Mozdzierz |
| 8,628,545 B2 | | 1/2014 | Cabrera et al. |
| 2004/0133189 A1 | * | 7/2004 | Sakurai ................... A61B 34/70 606/1 |
| 2004/0186376 A1 | | 9/2004 | Hogg et al. |
| 2005/0033201 A1 | * | 2/2005 | Takahashi ...... A61B 17/320068 601/2 |
| 2008/0167671 A1 | * | 7/2008 | Giordano ......... A61B 17/07207 606/167 |
| 2008/0237083 A1 | | 10/2008 | Mahaffy et al. |
| 2008/0262654 A1 | * | 10/2008 | Omori .................... A61B 90/96 700/245 |
| 2009/0314821 A1 | | 12/2009 | Racenet |
| 2011/0121049 A1 | | 5/2011 | Malinouskas et al. |
| 2011/0137116 A1 | | 6/2011 | Wehrstein et al. |
| 2011/0313894 A1 | * | 12/2011 | Dye ...................... A61B 90/98 705/28 |
| 2012/0046738 A1 | | 2/2012 | Lau et al. |
| 2012/0089131 A1 | * | 4/2012 | Zemlok ............ A61B 17/07207 606/1 |
| 2013/0184730 A1 | * | 7/2013 | Beardsley ........ A61B 17/07207 606/174 |
| 2013/0206814 A1 | | 8/2013 | Morgan et al. |
| 2013/0324979 A1 | | 12/2013 | Nicholas et al. |
| 2014/0021087 A1 | | 1/2014 | Adler et al. |
| 2014/0305988 A1 | * | 10/2014 | Boudreaux .......... A61B 17/068 227/175.3 |

OTHER PUBLICATIONS

Extended European Search Report, dated Oct. 22, 2015, corresponding to European Application No. 15172511.6; 6 total pages.

\* cited by examiner

DISPOSABLE HOUSINGS FOR ENCASING HANDLE ASSEMBLIES

CROSS-REFERENCE TO RELATED APPLICATIONS

This application claims the benefit of and priority to U.S. Provisional Patent Application No. 62/013,607, filed Jun. 18, 2014, the entire disclosure of which is incorporated by reference herein.

BACKGROUND

1. Technical Field

The present disclosure relates to disposable housings configured to encase a motor operable, inner core handle assembly. More specifically, the present disclosure relates to a surgical instrument system including disposable housings selected for use for a particular surgical procedure by matching a color of a disposable housing with a color of an adapter assembly and/or a color of an end effector.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like including an end effector disposed at an end thereof that are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical attachments, such as, for example, surgical loading units or end effectors, to establish a mechanical and/or electrical connection therebetween. Each end effector and/or adapter assembly has unique functional characteristics that correspond to a respective surgical procedure to be performed. Therefore, prior to performing the particular surgical procedure, one type of end effector and/or adapter assembly is selected based on the surgical procedure to be performed and attached to the handle assembly, which drives the functions of the selected end effector.

A need exists for a way to assist a practitioner in accurately and efficiently identifying and selecting an appropriate end effector and/or adapter assembly to be attached to a handle assembly for a particular surgical procedure to be performed.

SUMMARY

According to an aspect of the present disclosure, a disposable housing is provided. The disposable housing is configured to encase a motor operable, inner core handle assembly configured to drive an operation of a plurality of types of end effectors. The disposable housing includes a housing portion and a memory. The housing portion defines a cavity therein configured to receive the inner core handle assembly. At least a portion of the housing portion has a color that corresponds to a color of one type of end effector. The memory has stored therein at least one operating parameter for the inner core handle assembly.

In embodiments, the at least one operating parameter may be a speed of operation of a motor of the inner core handle assembly, an amount of power to be delivered by a motor of the inner core handle assembly during operation thereof, a selection of which motors of the inner core handle assembly are to be actuated, or types of functions of an end effector to be performed by the inner core handle assembly.

In embodiments, the color of at least a portion of the housing portion may correspond to one or more operating parameter.

It is contemplated that the memory has an identification code stored therein corresponding to one type of end effector. The disposable housing may further include a processor configured to determine when the identification code stored in the memory corresponds to a type of end effector operatively coupled to the inner core handle assembly.

In embodiments, the color of at least a portion of the housing portion may correspond to a color of one type of adapter assembly configured to operatively interconnect the one type of end effector and the inner core handle assembly. The at least one operating parameter may correspond to both the one type of end effector and the one type of adapter assembly.

It is envisioned that the housing portion may include a first housing portion and a second housing portion. The first and second housing portions may be movably coupled to one another such that the first and second housing portions are movable relative to one another between a closed, fully coupled configuration, and an open, partially detached configuration.

In another aspect of the present disclosure, a surgical instrument system is provided. The surgical instrument system includes a motor operable, inner core handle assembly, at least one type of end effector, and at least one disposable housing. The inner core handle assembly is capable of performing a plurality of operating parameters. The at least one type of end effector is configured to be operatively coupled to the inner core handle assembly. Each type of end effector has at least a substantially discrete color associated therewith and has at least one discrete function associated therewith. The at least one disposable housing includes a housing portion and a memory. The housing portion defines a cavity therein configured to receive the inner core handle assembly. At least a portion of the housing portion has a color corresponding to the color of one type of end effector. The memory has stored therein at least one operating parameter for the inner core handle assembly. The at least one operating parameter for the inner core handle assembly is specific to the type of end effector operatively coupled to the inner core handle assembly.

In embodiments, the surgical instrument system may further include at least one type of adapter assembly configured to operatively interconnect the inner core handle assembly and the at least one type of end effector. The color of at least a portion of the housing portion may correspond to a color of the at least one type of adapter assembly. The at least one operating parameter may correspond to both the at least one type of end effector and to the at least one type of adapter assembly.

It is envisioned that the memory may have an identification code stored therein corresponding to the at least one type of end effector. The at least one disposable housing may further include a processor configured to determine when the identification code stored in the memory corresponds to the at least one type of adapter assembly.

In some embodiments, the at least one type of end effector may include a plurality of types of end effectors each having a different color from one another. The at least one disposable housing may include a plurality of disposable housings each having a different color from one another. The color of each disposable housing may correspond to the color of one type of end effector. The memory of each disposable housing may have stored therein an identification code corresponding to one type of end effector. The at least one operating parameter stored in the memory of each disposable housing may be different from one another such that the inner core handle assembly operates differently based on the disposable housing by which it is encased.

In embodiments, the housing portion may include a first housing portion and a second housing portion. The first and second housing portions may be movably coupled to one another such that the first and second housing portions are movable relative to one another between a closed, fully coupled configuration, and an open, partially detached configuration.

In yet another aspect of the present disclosure, a method of configuring a hand-held, powered surgical instrument is provided. The method includes providing a motor operable, inner core handle assembly capable of performing a plurality of operating parameters; providing a plurality of disposable housings, each disposable housing of the plurality of disposable housings having at least a substantially discrete color associated therewith and including a memory having stored therein at least one operating parameter of the inner core handle assembly; providing a plurality of types of end effectors, each type of end effector having at least a substantially discrete color associated therewith; selecting one disposable housing of the plurality of disposable housings; inserting the inner core handle assembly within the selected one disposable housing; selecting one type of end effector of the plurality of types of end effectors based on the color of the selected one disposable housing; and operatively coupling the selected one type of end effector to the selected one disposable housing.

In embodiments, the method may further include operating the hand-held, powered surgical instrument in accordance with the at least one operating parameter.

It is contemplated that the color of each disposable housing may correspond to a different operating parameter of the at least one operating parameter.

In embodiments, the method may further include determining when the identification code corresponds to the selected one type of end effector coupled to the disposable housing. The method may further include at least one of: disabling operation of the inner core handle assembly when the identification code does not correspond to the selected one type of end effector coupled to the disposable housing; or enabling operation of the inner core handle assembly when the identification code corresponds to the selected one type of end effector coupled to the disposable housing.

In embodiments, the memory of each disposable housing may have a subset of operating parameters of the inner core handle assembly. Each operating parameter of the subset of operating parameters may correspond to one type of surgical procedure. The method may further include activating the subset of operating parameters upon the insertion of the inner core handle assembly within the selected one disposable housing.

In yet another aspect of the present disclosure, another method of configuring a hand-held, powered surgical instrument is provided. The method includes selecting a particular surgical procedure to be performed; providing a motor operable, inner core handle assembly capable of performing a plurality of operating parameters; providing a plurality of disposable housings, each disposable housing of the plurality of disposable housings having at least a substantially discrete color associated therewith and including a memory having stored therein at least one operating parameter of the inner core handle assembly; providing a plurality of types of end effectors, each type of end effector having at least a substantially discrete color associated therewith; selecting one type of end effector of the plurality of types of end effectors suited for performing the selected surgical procedure; selecting one disposable housing of the plurality of disposable housings based on the color of the selected one type of end effector; inserting the inner core handle assembly within the selected one disposable housing; and operatively coupling the selected one type of end effector to the selected one disposable housing.

In embodiments, upon the inserting of the inner core handle assembly within the selected one disposable housing, the inner core handle assembly may receive, from the memory of the selected one disposable housing, operating parameters by which the inner core handle assembly will operate. The operating parameters may include: a set of parameters tailored for operation of the selected one type of end effector; and a subset of parameters tailored for the selected surgical procedure.

It is envisioned that the method may further include: selecting an adapter assembly having a same color as the selected one type of end effector and the selected one type of disposable housing; and operatively connecting the selected adapter assembly to the inner core handle assembly and the selected one type of end effector.

BRIEF DESCRIPTION OF THE DRAWINGS

Embodiments of the present disclosure are described herein with reference to the accompanying drawings, wherein.

DETAILED DESCRIPTION

Figure 1:
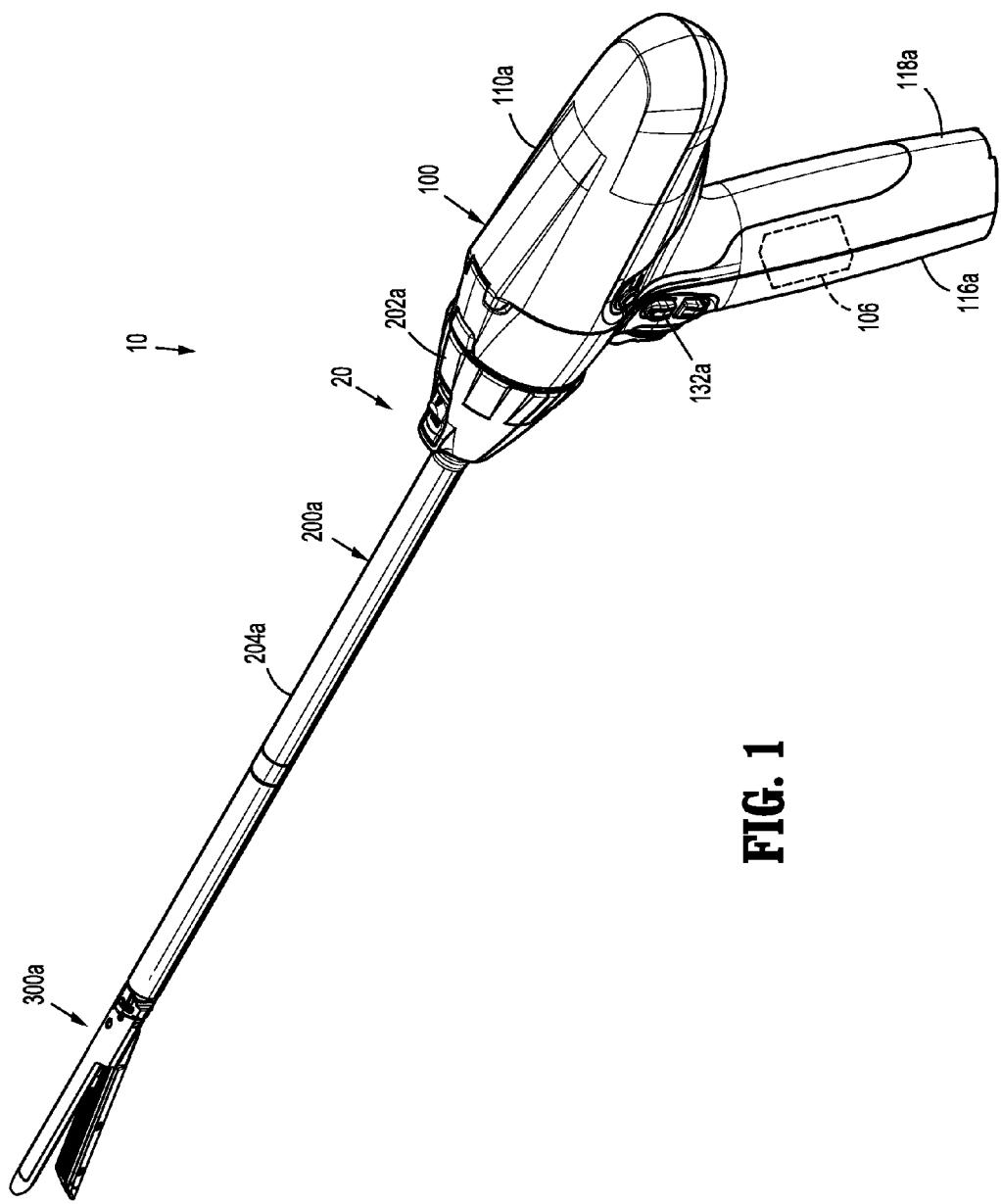
FIG. 1 is a perspective view of a hand-held, electromechanical surgical instrument system, in accordance with an embodiment of the present disclosure.

Embodiments of the presently disclosed electromechanical surgical instruments including inner core handle assemblies, adapter assemblies, and end effectors are described in detail with reference to the drawings, in which like reference numerals designate identical or corresponding elements in each of the several views. As used herein the term "distal" refers to that portion of the surgical instrument, adapter assembly, handle assembly, end effector or components thereof, farther from the user, while the term "proximal" refers to that portion of the surgical instrument, adapter assembly, handle assembly, end effector or components thereof, closer to the user.

Figure 3A:
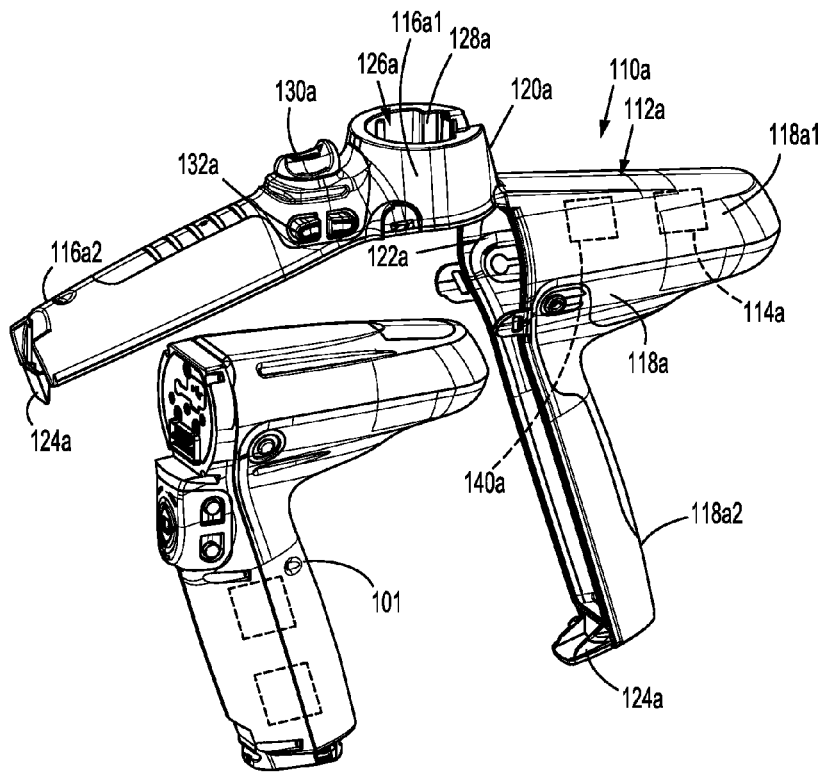
FIG. 3A is a perspective view of an embodiment of a disposable housing in an open configuration and the inner core handle assembly shown in FIG. 2.
Figure 3B:
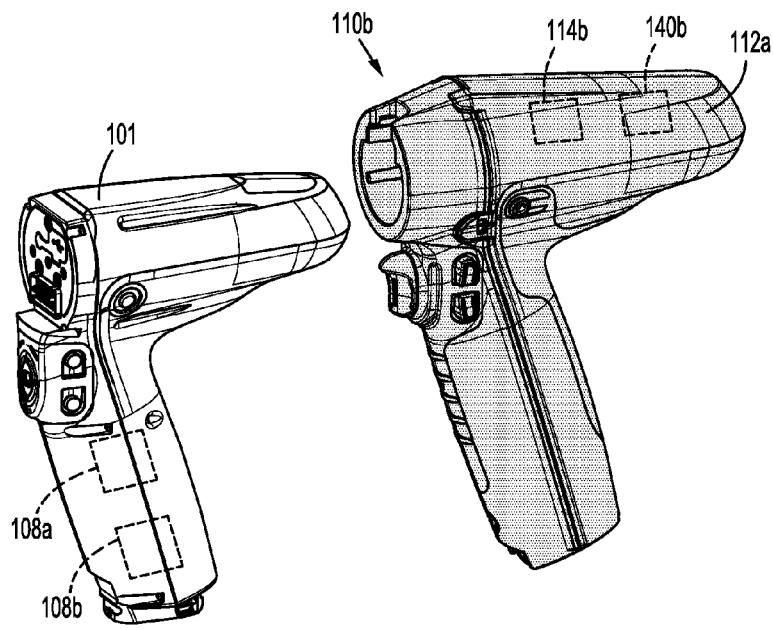
FIG. 3B is a perspective view of the disposable housing of FIG. 3A having a different color associated therewith and being in a closed configuration, and the inner core handle assembly shown in FIG. 2.
Figure 4A:
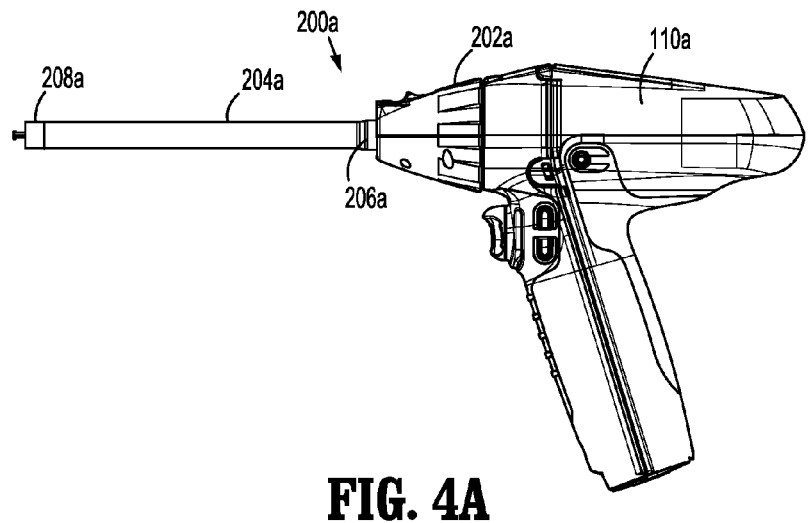
FIG. 4A is a side view of an embodiment of an adapter assembly shown operatively coupled to the surgical instrument system shown in FIG. 1.
Figure 4B:
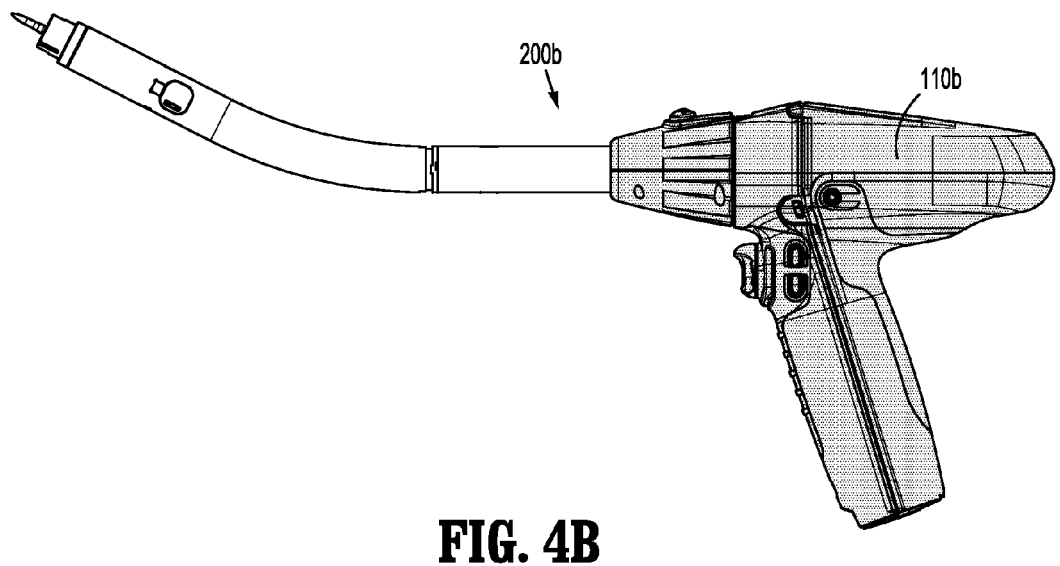
FIG. 4B is a side view of another embodiment of an adapter assembly shown operatively coupled to the surgical instrument system shown in FIG. 1.
Figure 5A:
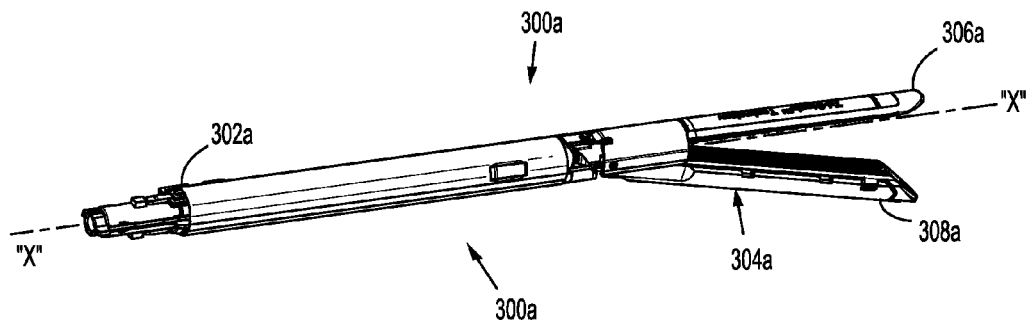
FIG. 5A is a perspective view of an embodiment of an end effector configured to be operatively coupled to the adapter assembly shown in FIG. 4A.
Figure 5B:
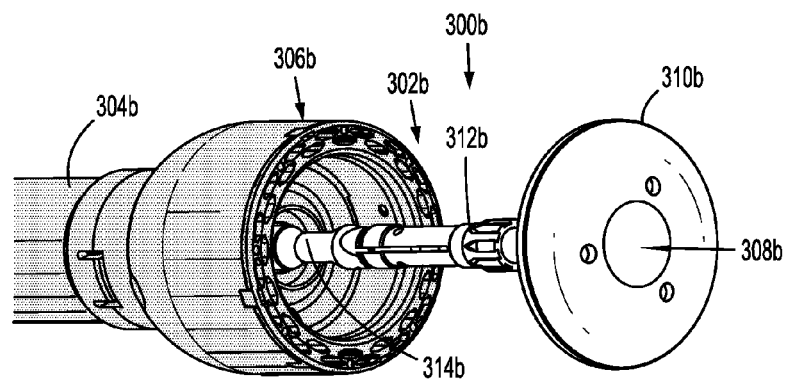
FIG. 5B is a perspective view of another embodiment of an end effector configured to be operatively coupled to the adapter assembly shown in FIG. 4B.

With reference to FIGS. 1-5B, a surgical instrument system is provided, such as, for example, an electromechanical surgical instrument system 10. System 10 includes a handle assembly 100, a plurality of types of adapter assemblies, for example, adapter assemblies 200a, 200b (FIGS. 4A and 4B), and a plurality of types of end effectors, for example, end effectors 300a, 300b (FIGS. 5A and 5B). Handle assembly 100 is configured for selective attachment thereto with any one of a number of adapter assemblies, for example, adapter assembly 200a (FIG. 4A) and/or adapter assembly 200b (FIG. 4B), and, in turn, each unique adapter assembly 200a or 200b is configured for selective connection with any number of surgical loading units or end effectors, such as, for example, end effector 300a (FIG. 5A) and/or end effector 300b (FIG. 5B), respectively. End effectors 300a, 300b and adapter assemblies 200a, 200b are configured for actuation and manipulation by handle assembly 100. Upon connecting one adapter assembly 200a or 200b to handle assembly 100 and one type of end effector 300a or 300b to the selected adapter assembly 200a or 200b, a powered, hand-held, electromechanical surgical instrument, generally designated as 20, is formed.

For a detailed description of the construction and operation of an exemplary electromechanical, hand-held, powered surgical instrument, reference may be made to International Publication No. WO 2009/039506 and U.S. Patent Application Publication No. 2011/0121049, the entire contents of all of which are incorporated herein by reference.

Figure 2:
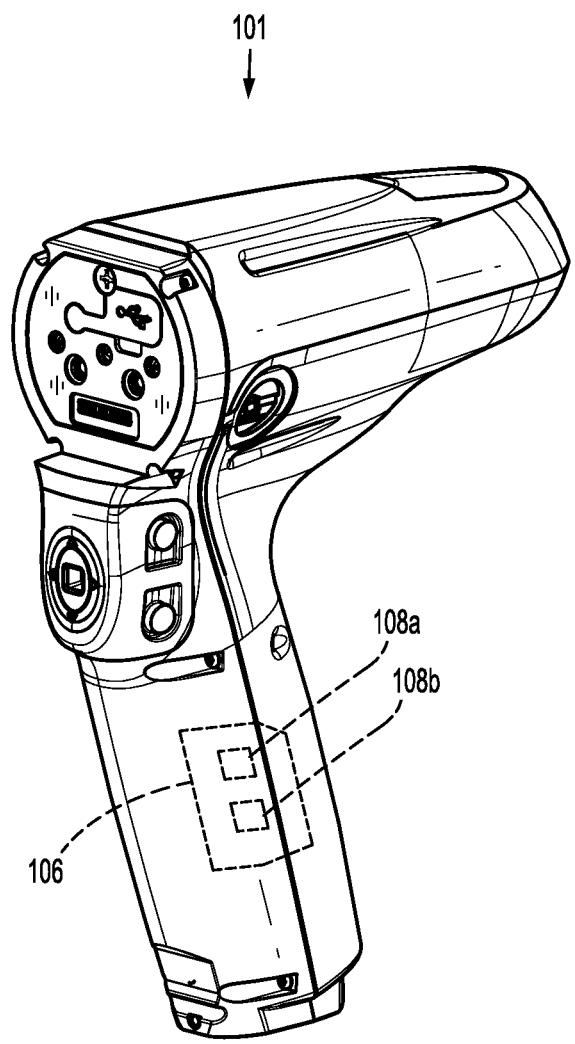
FIG. 2 is a perspective view of a motor operable, inner core handle assembly in accordance with an embodiment of the present disclosure.

With reference to FIGS. 1 and 2, handle assembly 100 includes an inner core handle assembly 101 and a disposable housing or shell 110a configured to selectively receive and encase inner core handle assembly 101. Inner core handle assembly 101 is motor operable and configured to drive an operation of a plurality of types of end effectors. Inner core handle assembly 101 has a plurality of sets of operating parameters (e.g., speed of operation of motors of inner core handle assembly 101, an amount of power to be delivered by motors of inner core handle assembly 101 to an adapter assembly, selection of motors of inner core handle assembly 101 to be actuated, functions of an end effector to be performed by inner core handle assembly 101, or the like). Each set of operating parameters of inner core handle assembly 101 is designed to drive the actuation of a specific set of functions unique to respective types of end effectors when an end effector is coupled to inner core handle assembly 101. For example, inner core handle assembly 101 may vary its power output, deactivate or activate certain buttons thereof, and/or actuate different motors thereof depending on whether end effector 300a or end effector 300b is coupled to inner core handle assembly 101, as described in greater detail below.

With specific reference to FIG. 2, inner core handle assembly 101 defines an inner housing cavity (not shown) therein in which a power-pack 106 is situated. Power-pack 106 is configured to control the various operations of inner core handle assembly 101. Power-pack 106 includes a plurality of motors 108a, 108b operatively engaged thereto. The rotation of motors 108a, 108b function to drive shafts and/or gear components (not shown) of adapter assembly 200a (FIG. 4A) and/or adapter assembly 200b (FIG. 4B) in order to drive the various operations of end effectors attached thereto, for example, end effectors 300a or 300b (FIGS. 5A and 5B).

In particular, when end effector 300a (FIG. 5A) is coupled to inner core handle assembly 101, motors of power-pack 106 are configured to drive shafts and/or gear components of adapter assembly 200a (FIG. 4A) in order to selectively move a tool assembly 304a of end effector 300a relative to a proximal body portion 302a of end effector 300a, to rotate end effector 300a about a longitudinal axis "X", to move a cartridge assembly 308a and an anvil assembly 306a of end effector 300a relative to one another, and/or to fire staples from within cartridge assembly 308a of end effector 300a. When end effector 300b (FIG. 5B) is coupled to inner core handle assembly 101, motors 108a, 108b of power pack 106 are configured to drive shafts and/or gear components of adapter assembly 200b (FIG. 4B) in order to selectively move an anvil 308b relative to a circular cartridge assembly 306b, to fire staples from within cartridge assembly 306b of end effector 300b, and to advance an annular knife blade from within circular cartridge assembly 306b.

With reference to FIGS. 1, 3A, and 3B, surgical instrument system 10 further includes a plurality of disposable housings, for example, disposable housing 110a (FIG. 3A) and/or a disposable housing 110b (FIG. 3B). In embodiments, surgical instrument system 10 includes a plurality of uniquely colored disposable housings, as described in greater detail below. Disposable housings 110a, 110b are configured to encase inner core handle assembly 101 thereby inhibiting surgical debris from penetrating and contaminating inner core handle assembly 101 during a surgical procedure. One of disposable housings 110a, 110b selectively encases inner core handle assembly 101 prior to use and may then be detached from inner core handle assembly 101 following use in order to be disposed of, or, in some instances, sterilized for re-use.

With reference to FIG. 3A, disposable housing 110a includes a housing portion 112a and a memory 114a supported by housing portion 112a. Housing portion 112a includes a first housing portion or distal half-section 116a and a second housing portion or proximal half-section 118a. Proximal half-section 118a is movably coupled to distal half-section 116a by a hinge 120a located along an upper edge of distal half-section 116a and proximal half-section 118a. Distal half-section 116a and proximal half-section 118a are pivotable relative to one another between a closed, fully coupled configuration, as shown in FIG. 3B, and an open, partially detached configuration, as shown in FIG. 3A. When joined, distal and proximal half-sections 116a, 118b define a cavity 122a therein in which inner core handle assembly 101, memory 114a, and a microprocessor 140a may be selectively situated.

Each of distal and proximal half-sections 116a, 118a includes a respective upper shell portion $116a_1$, $118a_1$ and a respective lower shell portion $116a_2$, $118a_2$. Lower shell portions $116a_2$, $118a_2$ define a snap closure feature 124a for selectively securing lower shell portions $116a_2$, $118a_2$ to one another and for maintaining housing portion 112a in the closed configuration. Distal half-section 116a and proximal half-section 118a of housing portion 112a may be fabricated from any suitable material, such as, for example, a polycarbonate.

Distal half-section 116a of housing portion 112a defines a connecting portion 126a configured to accept a corresponding drive coupling assembly (not shown) of adapter assembly 200a (FIG. 4A). Specifically, distal half-section 116a of housing portion 112a has a recess 128a that receives a proximal cap (not shown) of drive coupling assembly of adapter assembly 200a when adapter assembly 200a is mated to inner core handle assembly 101.

Distal half-section 116a of housing portion 112a supports a distal facing toggle control button 130a. Toggle control button 130a is capable of being actuated in a left, right, up, and down direction upon application of a corresponding force thereto or a depressive force thereto. Distal half-section 116a of housing portion 112a supports a right-side pair of control buttons (not shown) and a left-side pair of control button 132a. The right-side control buttons and left-side control buttons 132a are capable of being actuated upon application of a corresponding force thereto or a depressive force thereto.

Housing portion 112a of disposable housing 110a has a color associated therewith, including shading, black, or white. It is contemplated that housing portion 112a can have any suitable color associated therewith. The color of housing portion 112a corresponds to a color of one type of end effector. For example, housing portion 112a has a first color corresponding to end effector 300a (FIG. 3A), and a second color corresponding to end effector 300b (FIG. 5B). Similarly, adapter assembly 200a (FIG. 4A) may have a first color corresponding to end effector 300a, and adapter assembly 200b (FIG. 4B) may have a second color corresponding to end effector 300b.

In embodiments, at least a portion of an outer surface of housing portion 112a has a colored coating deposited thereon. In other embodiments, at least a portion of housing portion 112a is fabricated from a colored material. In one embodiment, at least a portion of housing portion 112a may have a colored pattern, design, or other indicia.

Accordingly, each disposable housing 110a, 110b, of the plurality of disposable housings, has a discrete color that matches a discrete color of one type of adapter assembly 200a, 200b and/or one type of end effector 300a, 300b, as described in greater detail below. In this way, each disposable housing 110a, 110b corresponds to one type of adapter assembly and/or one type of end effector.

With continued reference to FIGS. 3A and 3B, disposable housings 110a, 110b each include a memory 114a, 114b, respectively. It is contemplated that memories 114a, 114b may be non-volatile memories, such as, for example, electrically erasable programmable read-only memories. Memories 114a, 114b have stored therein discrete operating parameters of inner core handle assembly 101 that correspond to the operation of one type of end effector, for example, end effectors 300a or 300b, and/or one type of adapter assembly, for example, adapter assemblies 200a or 200b. The operating parameter(s) stored in memories 114a, 114b can be at least one of: a speed of operation of motors 108a, 108b of inner core handle assembly 101; an amount of power to be delivered by motors 108a, 108b of inner core handle assembly 101 during operation thereof; which motors 108a, 108b of inner core handle assembly 101 are to be actuated upon operating inner core handle assembly 101; types of functions of end effectors to be performed by inner core handle assembly 101; or the like.

The operating parameter(s) stored in memories 114a, 114b of each respective disposable housing 110a, 110b is different for each disposable housing 110a, 110b, such that inner core handle assembly 101 is directed to operate differently based on the particular disposable housing 110a, 110b by which it is encased, as described in greater detail below. Accordingly, one discrete color of a disposable housing corresponds to discrete operating parameter(s) (corresponding to particular end effectors and/or particular surgical procedures to be performed) stored in the memory of the disposable housing in which the memory is situated.

Memories 114, 114b of respective disposable housings 110a, 110b each further include a subset of operating parameters of inner core handle assembly 101. As briefly mentioned above, each subset of operating parameters may also correspond to one type of surgical procedure to be performed by surgical instrument 20, for example, transection or resection of tissue/organs, occlusion of tissue/organs in thoracic and abdominal procedures, or fastening of tissue/organs in anastomoses. Either upon insertion of inner core handle assembly 101 within the cavity of a selected disposable housings 110a or 110b, or upon selection by a clinician or surgeon, the subset of operating parameters corresponding to the selected disposable housing 110a or 110b is activated, such that inner core handle assembly 101 is adapted or configured to be used in the selected surgical procedure.

Memories 114a, 114b of respective disposable housings 110a, 110b also have a discrete identification code or serial number stored therein that corresponds to one type of end effector and/or one type of adapter assembly. The identification code stored in memories 114a, 114b indicates the type of end effector and/or adapter assembly to which the disposable housing 110a or 110b is intended to be used.

Disposable housings 110a, 110b each further include a processor, for example, a microprocessor 140a, 140b. Microprocessors 140a, 140b are configured to determine if and when the identification code stored in respective memories 114a, 114b corresponds to the type of end effector and/or the type of adapter assembly that is operatively coupled to inner core handle assembly 101. Microprocessors 140a, 140b of respective disposable housings 110a, 110b are configured to disable operation of inner core handle assembly 101 when the identification code stored in respective memories 114a, 114b does not correspond to a particular type of end effector and/or adapter assembly coupled to inner core handle assembly 101. For example, if the identification code stored in memory 114a corresponds to an endo-gastrointestinal anastomosis end effector 300a (see FIG. 5A) and, if a circular end-to-end anastomosis end effector 300b (see FIG. 5B) is coupled to inner core handle assembly 101, a negative identification will be made by processor 140a and inner core handle assembly 101 will be rendered inoperable.

Microprocessors 140a, 140b of respective disposable housings 110a, 110b are further configured to allow inner core handle assembly 101 to be operable when the identification code stored in respective memories 114a, 114b corresponds to a particular type of end effector and/or adapter assembly coupled to inner core handle assembly 101. For example, if the identification code of memory 114b corresponds to a circular end-to-end anastomosis end effector 300b (FIG. 5B) and a circular end-to-end anastomosis end effector is coupled to inner core handle assembly 101, a positive identification will be made by processor 140b and inner core handle assembly 101 will be enabled for operation.

With reference to FIGS. 4A and 4B, surgical instrument system 10 further includes a plurality of adapter assemblies, for example, adapter assemblies 200a and 200b, as mentioned above. It is contemplated that surgical instrument system 10 may include various alternately configured adapter assemblies suitable for coupling inner core handle assembly 101 to various types of end effectors.

With reference to FIG. 4A, adapter assembly 200a is configured to couple an endo-gastrointestinal anastomosis end effector, for example, end effector 300a (FIG. 5A) to inner core handle assembly 101. Adapter assembly 200a includes a knob housing 202a and an elongated body 204a extending from a distal end of knob housing 202a. Knob housing 202a and elongated body 204a are configured and dimensioned to house the components of adapter assembly 200a. Elongated body 204a is dimensioned for endoscopic insertion. For example, elongated body 204a is passable through a typical trocar port, cannula, or the like. Knob housing 202a is dimensioned to not enter the trocar port, cannula, or the like. Elongated body 204a of adapter assembly 200a has a proximal portion 206a coupled to knob housing 202a and a distal portion 208a configured to be coupled to end effector 300a (FIG. 5A).

With reference to FIG. 4B, another embodiment of an adapter assembly is provided, similar to adapter assembly 200a, and is designated 200b. Adapter assembly 200b is configured to couple an end to end anastomosis end effector, for example, end effector 300b (FIG. 5B) to inner core handle assembly 101.

With continued reference to FIGS. 4A and 4B, adapter assemblies 200a, 200b each have a discrete color associated therewith. The color of each adapter assembly 200a, 200b may correspond to or match with the discrete color of one respective disposable housing 110a or 110b so that a clinician or surgeon can visually identify the type of adapter assembly to be used with a particular disposable housing. Alternatively, the color of each adapter assembly 200a, 200b may correspond to or match with the discrete color of one respective end effector 300a, 300b so that a clinician or surgeon can visually identify the type of adapter assembly to be used with a particular end effector.

With reference to FIGS. 5A and 5B, surgical instrument system 10 further includes a plurality of end effectors, for example, end effectors 300a and 300b, as mentioned above. It is contemplated that surgical instrument system 10 may include various alternately configured end effectors suitable for connection to various respective adapter assemblies. For example, surgical instrument system 10 may include at least one of a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device, a stitching device, a tack applying device, or any other type of surgical instrument. Such surgical instruments are described, for example, in U.S. Pat. Nos. 6,315,184; 6,443,973; 6,264,087; 6,348,061; 6,716,233; 6,533,157; 6,491,201; 6,488,197; 7,931,660; and 8,628,545, the contents of each of which is expressly incorporated herein in its entirety by reference.

With reference to FIG. 5A, end effector 300a extends between a proximal body portion 302a configured to be connected to distal end 208a of adapter assembly 200a (FIG. 4A) and a distal tool assembly 304a. End effector 300a may be rotatable relative to distal end 208a of adapter assembly 200a about longitudinal axis "X." Tool assembly 304a includes an anvil assembly 306a and a cartridge assembly 308a. Cartridge assembly 308a includes a stapling and cutting cartridge. Cartridge assembly 308a and anvil assembly 306a are pivotable relative to one another to clamp or unclamp material, such as, for example, tissue, therebetween.

Reference may be made to U.S. Patent Publication No. 2009/0314821, filed on Aug. 31, 2009, entitled "TOOL ASSEMBLY FOR A SURGICAL STAPLING DEVICE," for a detailed discussion of the construction and operation of end effector 300a, the contents of which is expressly incorporated herein in its entirety by reference.

With reference to FIG. 5B, another embodiment of an end effector is provided, and is designated 300b. End effector 300b includes an operable circular head assembly 302b and an elongated body portion 304b. Head assembly 302b is mounted on a distal end of elongate body portion 304b and generally includes a circular staple cartridge 306b mounted to elongate body portion 304b and a circular anvil assembly 308b which is movable relative to staple cartridge 306b. Anvil assembly 308b includes an anvil plate 310b and an anvil shaft 312b extending proximally from anvil plate 310b. A movable anvil retainer or retention shaft 314b extends out of elongate body portion 304b and is provided to removably receive anvil shaft 312b. Anvil assembly 308b is movable relative to staple cartridge 306b to grasp and compress tissue therebetween.

Reference may be made to U.S. Pat. No. 8,490,850, filed on Apr. 29, 2011, entitled "CIRCULAR STAPLER WITH CONTROLLER TISSUE COMPRESSIONS," for a detailed discussion of the construction and operation of end effector 300b, the contents of which is expressly incorporated herein in its entirety by reference.

With continued reference to FIGS. 5A and 5B, as briefly mentioned above, end effectors 300a, 300b each have a discrete color associated therewith. The color of each end effector 300a, 300b corresponds to or matches with the discrete color of one respective disposable housing 110a or 110b and the discrete color of adapter assemblies 200a or 200b, so that a clinician or surgeon can visually identify the type of end effector to be used with a particular disposable housing and adapter assembly.

In assembly, operation, and use, a particular surgical procedure is selected, such as, for example, a thoracic surgery having a unique and/or specific set of surgical operating parameters/requirements/tasks. Accordingly, a desired/necessary end effector, e.g., end effector 300a, is selected from the plurality of end effectors available for use in order to achieve the surgical operating parameter/requirement/task. One disposable housing of the plurality of disposable housings is selected based on its color. Specifically, a disposable housing that has the same color as end effector 300a is selected, e.g., disposable housing 110a. Inner core handle assembly 101 is then inserted within the cavity of the selected disposable housing 110a. Upon inserting inner core handle assembly 101 within disposable housing 110a, inner core handle assembly 101 receives, from memory 114a of disposable housing 110a, the parameter(s) by which inner core handle assembly 101 will operate during use, including, for example, a set of parameters tailored for the operation of end effector 300a and a subset of parameters tailored for the thoracic surgery.

An adapter assembly is then selected that matches or has the same color as end effector 300a and disposable housing 110a. It is contemplated that an adapter assembly may be selected prior to the selection of a disposable housing and/or end effector. The selected adapter assembly, for example, adapter assembly 200a, is operatively connected to inner core handle assembly 101, and end effector 300a is operatively connected to adapter assembly 200a, such that surgical instrument 20 is fully assembled. Upon coupling adapter assembly 200a and end effector 300a with inner core handle assembly 101, processor 140a of disposable housing 110a matches the identification code stored in memory 114a of disposable housing 110a with end effector 300a to determine that end effector 300a is the appropriate type of end effector to be used with the selected disposable housing 110a. Inner core handle assembly 101 is then ready for operation in accordance with the set of operating parameter(s) and the subset of operating parameters stored in memory 114a of disposable housing 110a.

Following the surgical procedure, snap closure feature 124a of lower shell portion 116a$_2$ of distal half-section 116a is disengaged from snap closure feature 124a of lower shell portion 118a$_2$ of proximal half-section 118a, and distal half-section 116a is pivoted, about hinge 120a, away from proximal half-section 118a to open housing portion 112a. With housing portion 112a open, inner core handle assembly 101 is removed from cavity 122a of housing portion 112a (specifically from proximal half-section 118a of housing portion 112a), and disposable housing 110a is discarded. Inner core handle assembly 101 is then disinfected and cleaned.

It will be understood that various modifications may be made to the embodiments of the presently disclosed surgical instrument system 10 and components thereof. Therefore, the above description should not be construed as limiting, but merely as exemplifications of embodiments. Those skilled in the art will envision other modifications within the scope and spirit of the present disclosure.

The invention claimed is:

1. A surgical instrument system, comprising:
a motor operable, inner core handle assembly capable of performing a plurality of operating parameters;
a plurality of types of end effectors each having a different color from one another, each type of end effector configured to be selectively, operatively coupled to the inner core handle assembly, wherein each type of end effector has at least one discrete function associated therewith; and
a plurality of disposable housings, each disposable housing including:
a housing portion defining a cavity therein configured to encase the inner core handle assembly, wherein the housing portion of each of the plurality of disposable housings has a different color from one another, the color of each housing portion being the same as the color of a corresponding type of end effector; and
a memory having, stored therein, at least one operating parameter for the inner core handle assembly, wherein the at least one operating parameter for the inner core handle assembly corresponds to the type of end effector operatively coupled to the inner core handle assembly.

2. The surgical instrument system according to claim 1, wherein the at least one operating parameter of each of the plurality of disposable housings is selected from the group consisting of a speed of operation of a motor of the inner core handle assembly, an amount of power to be delivered by a motor of the inner core handle assembly during operation thereof, a selection of which motors of the inner core handle assembly are to be actuated, and types of functions of the corresponding type of end effector to be activated by the inner core handle assembly.

3. The surgical instrument system according to claim 1, wherein the color of the housing portion of each of the plurality of disposable housings corresponds to the at least one operating parameter of a discrete disposable housing of the plurality of disposable housings, the at least one operating parameter of each of the plurality of disposable housings is customized for the operation of the corresponding type of end effector.

4. The surgical instrument system according to claim 1, further including a plurality of types of adapter assemblies, wherein each of the plurality of types of adapter assemblies is configured to selectively, operatively interconnect the inner core handle assembly and the corresponding type of end effector of the plurality of types of effectors.

5. The surgical instrument system according to claim 4, wherein the color of the housing portion of each of the plurality of disposable housings is the same as a color of a corresponding type of adapter assembly of the plurality of types of adapter assemblies.

6. The surgical instrument system according to claim 5, wherein the at least one operating parameter of each of the plurality of disposable housings corresponds to both a discrete type of end effector of the plurality of types of end effectors and to a discrete type of adapter assembly of the plurality of types of adapter assemblies.

7. The surgical instrument system according to claim 6, wherein the memory of each of the plurality of disposable housings has an identification code stored therein each corresponding to the discrete type of adapter assembly of the plurality of types of adapter assemblies.

8. The surgical instrument system according to claim 7, wherein each of the plurality of disposable housings further includes a processor configured to determine when the identification code stored in the memory corresponds to the discrete type of adapter assembly.

9. The surgical instrument system according to claim 1, wherein the memory of each disposable housing of the plurality of disposable housings has, stored therein, an identification code corresponding to one type of end effector of the plurality of types of end effectors.

10. The surgical instrument system according to claim 9, wherein the at least one operating parameter stored in the memory of each disposable housing of the plurality of disposable housings is different from one another such that the inner core handle assembly operates differently based on the disposable housing the inner core handle assembly is encased in.

11. The surgical instrument system according to claim 1, wherein the housing portion of each of the plurality of disposable housings includes a first housing portion and a second housing portion, the first and second housing portions being movably coupled to one another such that the first and second housing portions are movable relative to one another between a closed, fully coupled configuration, and an open, partially detached configuration.

* * * * *